United States Patent [19]

Braid

[11] Patent Number: 4,457,868
[45] Date of Patent: Jul. 3, 1984

[54] METHOD FOR ESTERIFICATION

[75] Inventor: Milton Braid, Haddonfield, N.J.

[73] Assignee: Mobil Oil Corporation, New York, N.Y.

[21] Appl. No.: 298,666

[22] Filed: Sep. 2, 1981

[51] Int. Cl.³ .............................................. C11C 3/10
[52] U.S. Cl. ................................. 260/404; 260/410.5; 260/410.6; 260/410.9 R; 560/71; 560/100; 560/108; 560/193; 560/194; 560/217; 560/234
[58] Field of Search ................. 260/404, 410.5, 410.6, 260/410.9 R; 560/193, 194, 217, 234

[56] References Cited

U.S. PATENT DOCUMENTS 2,822,348  2/1958  Haslam ........................... 560/234 X
3,784,578  1/1974  Swodenk et al. ............... 560/234 X
4,283,565  8/1981  Bernhardt et al. .............. 560/234 X

OTHER PUBLICATIONS

Stapp et al., J. Org. Chem. 24, pp. 1798–1800, (1959).

Primary Examiner—Thomas A. Waltz
Attorney, Agent, or Firm—Alexander J. McKillop; Michael G. Gilman; Claude E. Setliff

[57] ABSTRACT

A method for conducting transesterification reactions employing a catalyst system comprising metallic sodium and aluminum isopropoxide which provides a facile, high yield, means for producing compounds such as esters of alkyl- and alkyloxy-substituted arylamines.

17 Claims, No Drawings

METHOD FOR ESTERIFICATION

BACKGROUND OF THE INVENTION

1. Field of the Invention

This invention relates to esterification techniques and, more particularly, to improved esterification procedures involving the use of unique catalytic systems.

2. Summary of the Prior Art

Ester interchange reactions are well known in the art and, generally speaking, comprise the reaction of an ester with another compound to form an ester different from the reactant ester. Such ester interchange reactions have been referred to by various names including, transesterification, ester exchange, re-esterification, etc.

There are three basic types of reactions falling within the above referred-to categories. All are equilibrium reactions and may be summarized in equation form as follows:

$$RCOOR^1 + R^2COOR^3 \rightleftharpoons R^2COOR^1 + RCOOR^3$$

$$RCOOR^1 + R^2OH \rightleftharpoons RCOOR^2 + R^1OH$$

$$RCOOR^1 + R^2COOH \rightleftharpoons R^2COOR^1 + RCOOH$$

where the R's are any suitable and stable organic moiety. This invention is primarily directed to reactions of the type described by equation 2. For example, hydroxyalkoxydiarylamines such as 4-(3-hydroxypropoxy)diphenylamine can be esterified with methyl hexanoate by similar reaction to p-anilinophenoxypropyl hexanoate. Methanol is released in this reaction and is removed as formed.

In the past, ester interchange reactions as set forth above have had many practical uses and, in fact, have provided an important approach to the synthesis of a variety of useful products. For example, such reactions have been used for the acid group exchange of glycerol esters with mixtures of fatty acids, for effecting ester-ester interchange between aromatic carboxylic esters of monohydric alcohols (e.g., dimethyl phthalate) and low or high molecular weight aliphatic carboxylic acid esters of polyhydric alcohols such as glycerol (triacetin, trilinolein), etc. One significant limitation on the versatility of such ester exchange techniques has been, however, the nature of the particular catalyst utilized in the reaction. For example, many of the prior art catalysts have been acids or bases which have been unsatisfactory with certain compounds with which they react. Other catalysts, less reactive, have required reaction conditions such as high temperatures under which reactants can decompose or rearrange. Still others have often presented difficult separation problems after the reaction is completed or have been short lived and, due to their nature, have not been readily regenerable.

In the case of the reactant systems of this invention, acid catalysts, e.g. sulfuric acid or hydrogen chloride and basic catalysts, e.g. sodium methoxide, sodium metal, aluminum t-butoxide and the like, individually or in combination, have not been effective in promoting ester interchange.

SUMMARY OF THE INVENTION

In accordance with the present invention, it has now been discovered that ester exchange reactions as set forth herein may be carried out in an extremely satisfactory manner which on the one hand is facile and on the other results in high product yield when conducted in the presence of the unique catalyst system embodied herein. This catalyst system, in contradistinction to the prior art, uses a combination of metallic sodium and aluminum isopropoxide. Each has been used individually in other ester exchange processes, but they have been found to be individually ineffective in the ester exchange reactions of this invention. Furthermore, applicant is unaware of any patent, publication or teaching wherein this unique but essential combination is taught, suggested or disclosed.

As hereinbefore suggested, in accordance with one aspect of the present invention, it has been found that certain desired ester interchange reactions will not proceed in the presence of individual, known transesterification catalysts. However, it has been unexpectedly discovered that transesterification, for example the reaction of 4-(3-hydroxypropoxy)diphenylamine with methyl hexanoate, which could not be effected using sodium metal and sodium methoxide, individually, or in combination with aluminum t-butoxide, may now be unexpectedly accomplished using a combination of sodium metal and aluminum isopropoxide. Similarly, transesterification of 4-(6-hydroxyhexoxy)diphenylamine with methyl hexanoate which proceeded only slowly using aluminum isopropoxide is given a dramatically increased reaction rate upon addition of sodium metal to the reaction mixture.

DESCRIPTION OF SPECIFIC EMBODIMENTS

The ester exchange reactions which may be carried out in accordance with this invention are as noted above generally of the type described by equation 2. As is well known to those of ordinary skill in the art, R,($R^1$, $R^2$, $R^3$) may be selected from a wide group of organic moieties. For example R may be aliphatic (including such as those derived from alkanes, alkenes or alkynes), cycloaliphatic, aromatic, alkylated aromatic and the like.

The esters suitable for use herein generally may be any appropriate ester of a carboxylic acid. A non-exhaustive list of examples of suitable acids include acetic, benzoic, butyric, heptanoic, formic, isobutyric, isovaleric, naphthoic, propionic, salicylic, valeric, acrylic, crotonic, hydrosorbic, undecylenic, propiolic, laurolenic, hydrocinnamic, benzoylacetic, furoic, abietic, caproic, caprylic, capric, lauric, pivalic, myristic, palmitic, p-phenyl benzoic, betanaphthoic, stearic, oleic, linoleic, linolenic, fumaric, maleic, malic, malonic, oxalic, phthalic, terephthalic, pyrotartaric, succinic, tartaric, glutaric, adipic, pimelic, suberic, azaleic, sebacic, apocamphoric, diphenic, naphthalene-1,2-dicarboxylic, furalmalonic, dilinoleic, citric, tricarballylic, aconitic, trilinoleic, hemimellitic, lactic, mandelic, ricinoleic, glycolic, hydracrylic, glyceric, quinec, caffeic, tropic, meconic, arachidic, behenic, lignoceric, myristoleic, palmitoleic, etc. Especially preferred are $C_1$ to $C_{20}$ alkyl carboxylic acids such as acetic, butyric, isobutyric, hexanoic, etc. The esters of such acids suitable for use herein are those prepared from hydroxyorganic compounds such as alcohols, diols, phenols, etc. A non-exhaustive list of examples includes methanol, ethanol, propanol, isopropyl alcohol, ethylene glycol, 1,4-butanediol, cyclohexanol, cyclohexane diol, phenol, cresol, etc. Preferred are esters of volatile alcohols such as methanol, ethanol, etc. Particularly suitable esters are methyl hexanoate, methyl octanoate, methyl pavalate and dimethyl suberate.

The hydroxyalkoxydiarylamines and hydroxyalkyldiarylamines which may be employed in the catalyzed transesterification method of the present invention may be represented by the following generic formula:

Ar NH Ar' ROH wherein Ar and Ar' may be phenyl, naphthyl or phenanthryl, R is hydroxy substituted alkyloxy or alkyl containing from 1 to 12 carbon atoms and may be straight or branched or may be cycloalkyloxy or alkyl-substituted cycloalkyl containing from 3 to 20 carbon atoms and the hydroxy substituent may be at any position in the said R group except where such positioning constitutes a tertiary alcohol.

Suitable hydroxyalkyldiarylamines and hydroxyalkoxydiarylamines include 4-(2-hydroxyethyl)diphenylamine, 4-(2-hydroxyethoxy)diphenylamine, 4-anilinobenzyl alcohol, N-4-(3-hydroxypropoxyphenyl)-1-naphthylamine, 4-(2-hydroxyhexoxy)diphenylamine, 4-(3-hydroxy-1-cyclohexyloxy)diphenylamine, and the like. Although any hydroxyalkyldiarylamine or hydroxyalkoxydiarylamine from the above non-exhaustive list or fairly suggested by it may be used, 4-(3-hydroxypropoxy)diphenylamine and 4-(6-hydroxyhexoxy)diphenylamine are preferred embodiments.

The catalyst system consists of metallic sodium and aluminum isopropoxide. Both are readily available from commercial sources. Generally they are used in a stoichiometric ratio of sodium to aluminum compound of from about 0.2 to 2.

The amount of catalyst used will vary depending upon specific reactants. However, esterification reactions of the type contemplated in general require from about 0.1 weight % to 4 weight % catalyst per total weight of reactants. Preferably the esterification is effected by catalyst mixtures falling within the following weight % ratios: 0.2 to 2.

In general the process comprises reacting in a suitable reaction medium from about 0.5 mol to about 1 mole of hydroxyalkyldiarylamine or hydroxyalkoxydiarylamines to 1 mol of ester. Preferentially about 0.5 to 0.9 are used. The process may be accomplished batchwise or in a comtinuous method under atmospheric, subatmospheric or superatmospheric pressure. The actual reaction conditions under which the esterification reactions in accordance with the present invention are carried out will vary depending, inter alia, upon the specific nature of the starting materials. Generally speaking the esterification reactions are carried out at temperatures of from 80° to about 200° C. and at any convenient pressure. Preferably temperatures are controlled within 120° to 180° C. and pressures from atmospheric to 200 psi.

The following specific examples are intended to illustrate embodiments of the present invention and accordingly are not intended to be construed in a limiting manner.

EXAMPLE 1

To a mixture of 4-(3-hydroxypropoxy)diphenylamine (24.3 g) and methyl hexanoate (13.0 g) heated at 100° C. there was added a small amount of sodium methoxide freshly prepared catalyst (about 0.2 g) and the mixture was heated for 4.25 hours at 120°-140° C. No conversion to transesterified product could be detected by gas chromatography.

To the reaction mixture more methyl hexanoate (30 g) was added and then sodium metal (0.1 g) and heating at 140° C. was continued for 3.25 hours. No transesterified product could be detected by gas chromatography. Addition of aluminum t-butoxide (0.1 g) and further heating also showed no evidence of transesterification. Aluminum isopropoxide (0.1 g) was added and the mixture was heated for 1 hour during which transesterification began and proceeded briskly as detected by gas chromatography monitoring. From this reaction there was obtained the transesterified product 3-(4-anilinophenoxy)propyl hexanoate m.p. 50°-51° C.

Analysis: Calc'd for $C_{21}H_{27}NO_3$: C, 73.87; H, 7.97; N, 4.10. Found: C, 74.23; H, 7.85; N, 4.08.

EXAMPLE 2

A mixture of 4-(6-hydroxyhexoy)diphenylamine (28.5 g), methyl hexanoate (39 g) and aluminum isopropoxide (0.3 g) was heated at 130°-150° C. for about 2.5 hours. Gas chromatography indicated minor, if any, transesterification. Aluminum isopropoxide (0.2 g) was added and the mixture was heated at 150° C. for 0.5 hours without evidence of transesterification. Sodium metal (0.1 g) was added, and during heating at 145° C. for 3 hours substantial transesterification occurred. Additional increments of methyl hexanoate (total 26 g) aluminum isopropoxide (total 0.2 g) and sodium (total 0.2 g) were added followed by several more hours of heating at 140°-145° C. The product ester, 6-(4-anilinophenoxy)hexyl hexanoate was obtained from this reaction after work-up and column chromatography as a viscous oil.

Analysis: Calc'd for $C_{24}H_{33}NO_3$: C, 75.16; H, 8.67; N, 3.65. Found: C, 75.51; H, 8.65; N, 3.56.

EXAMPLE 3

A mixture of n-octanoic acid (28.8 g), 4-(3-hydroxypropoxy)diphenylamine (48.6 g), benzene (200 ml) and concentrated sulfuric acid (1 g) was refluxed for about 1 hour. No azeotropic distillation of water was noted. The reaction mixture was then saturated with hydrogen chloride and refluxed for about 4.5 hours with the azeotropic removal of a small amount of water. After work-up of this reaction there was obtained 1.1 g of the ester 3-(4-anilinophenoxy)propyl octanoate, m.p. 45°-46° C.

Analysis: Calc'd for $C_{23}H_{31}NO_3$: C, 74.76; H, 8.46; N, 3.79. Found: C, 74.66; H, 8.48; N, 3.78.

EXAMPLE 4

A mixture of 4-(6-hydroxyhexoxy)diphenylamine (28.5 g), methyl octanoate (47.5 g), aluminum isopropoxide (0.3 g) and sodium (0.1 g) was heated at 160°-170° C. for a total of 9 hours while stirring. The transesterification product, 6-(4-anilinophenoxy)hexyl octanoate (44 g) was obtained from this reaction as a crystalline solid, m.p. 42°-43° C. (recrystallized from 2-propanol.

Analysis: Calc'd for $C_{26}H_{37}NO_3$: C, 75.87; H, 9.06; N, 3.40. Found: C, 76.18; H, 8.75; N, 3.51.

EXAMPLE 5

A mixture of 4-(6-hydroxyphenoxy)diphenylamine (42.8 g) and dimethyl suberate (15.2 g) to which aluminum isopropoxide (0.2 g) and sodium metal (0.1 g) were added was heated at 160°-185° C. for a total of about 5 hours. The transesterification product di-6-(4-anilinophenoxy)hexyl suberate was obtained from this reaction as a crystalline solid (20 g recrystallized from 2-propanol) m.p. 90°-92° C.

Analysis: Calc'd for $C_{44}H_{56}O_6N_2$: C, 74.55; H, 7.96; N, 3.95. Found: C, 73.35; H, 7.61; N, 3.82.

EXAMPLE 6

A mixture of 4-(6-hydroxyphenoxy)diphenylamine (28.5 g), methyl pivalate (34.5 g), aluminum isopropoxide (0.3 g) and sodium metal (0.1 g) was heated at reflux. Gas chromatography showed transesterification occurring slowly. Most of the methyl pivalate was distilled from the mixture and the reaction temperature was raised to 175° C. The methyl pivalate was then readded to the mixture during 2 hours at 175°–190° C. The transesterified product 6-(4-anilinophenoxy)hexyl pivalate was obtained from this reaction as a crystalline solid (20 g after recrystallization from 2-propanol) m.p. 64°–65° C.

Analysis: Calc'd for $C_{23}H_{31}O_3N$: C, 74.76; H, 8.46; N, 3.79. Found: C, 73.59; H, 8.12; N, 4.07.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed:

1. A method for carrying out an ester interchange reaction between a carboxylic acid ester and a hydroxylamine of the formula

wherein Ar and Ar' are phenyl, naphthyl or phenanthryl and R is a $C_1$ to $C_{20}$ alkyl group or a $C_1$ to $C_{20}$ hydroxy-substituted alkoxy group comprising conducting said reaction in the presence of a minor amount of a catalyst system comprising a mixture of metallic sodium and aluminum isopropoxide.

2. The method of claim 1 wherein the stoichiometric ratio of sodium to aluminum isopropoxide varies from about 0.2 to about 2.0.

3. The method of claim 1 wherein R of said amine is an alkyl group.

4. The method of claim 1 wherein the hydroxyalkyldiarylamine is a hydroxy-$C_1$ to $C_{20}$-alkyldiphenylamine.

5. The method of claim 1 wherein said amine is selected from 4-(3-hydroxypropoxy)diphenylamine and 4-(6-hydroxyhexoxy)diphenylamine.

6. The method of claim 1 wherein said ester is derived from a $C_1$ to $C_{20}$ alkyl carboxylic acid or these acids substituted with a $C_1$ to $C_{20}$ alkyl group.

7. The method of claim 6 wherein said $C_1$ to $C_{20}$ alkyl carboxylic acid is acetic, butyric, isobutyric, hexanoic, heptanoic, octanoic or pivalic acid.

8. The method of claim 6 wherein said ester is methyl hexanoate.

9. The method of claim 6 wherein said ester is dimethyl suberate.

10. The method of claim 6 wherein said ester is methyl pivalate.

11. The method of claim 6 wherein said ester is methyl octanoate.

12. The method of claim 1 wherein the interchange reaction is between 4-(3-hydroxypropoxy)diphenylamine and methyl hexanoate.

13. The method of claim 1 wherein the interchange reaction is between 4-(6-hydroxyhexoxy)diphenylamine and methyl hexanoate.

14. The method of claim 1 wherein the interchange reaction is between 4-(3-hydroxypropoxy)diphenylamine and octanoic acid.

15. The method of claim 1 wherein the interchange reaction is between 4-(6-hydroxyhexoxy)diphenylamine and methyl octanoate.

16. The method of claim 1 wherein the interchange reaction is between 4-(6-hydroxyphenoxy)-diphenylamine and dimethyl suberate.

17. The method of claim 1 wherein the interchange reaction is between 4-(6-hydroxyphenoxy)diphenylamine and methyl pivalate.

* * * * *